United States Patent [19]

Janus

[11] Patent Number: 5,439,490
[45] Date of Patent: Aug. 8, 1995

[54] METHOD FOR USE IN A MULTIPLICATION PROCESS OF PLANTS AND A DEVICE FOR CARRYING OUT SAID METHOD

[75] Inventor: Edwin O. M. Janus, Gerwen, Netherlands

[73] Assignee: Plant Production Systems B.V., Helmond, Netherlands

[21] Appl. No.: 94,139

[22] PCT Filed: Jan. 28, 1992

[86] PCT No.: PCT/NL92/00020

§ 371 Date: Sep. 28, 1993

§ 102(e) Date: Sep. 28, 1993

[87] PCT Pub. No.: WO92/01344

PCT Pub. Date: Aug. 20, 1992

[30] Foreign Application Priority Data

Feb. 1, 1991 [WO] WIPO ............... PCT/NL91/00015

[51] Int. Cl.6 ................ A01G 3/00; A01G 7/00; A01H 4/00
[52] U.S. Cl. .................. 47/58; 435/240.45; 422/62; 83/401
[58] Field of Search .......... 435/240.45; 83/151, 83/410, 401; 47/58.18, 58.19, 58.27; 382/10, 22, 25, 44, 48; 348/47, 89, 91; 422/62

[56] References Cited

U.S. PATENT DOCUMENTS

| | | | |
|---|---|---|---|
| 4,285,258 | 8/1981 | Logan et al. | 83/410 |
| 4,395,699 | 7/1983 | Sternberg | 382/41 |
| 4,642,459 | 2/1987 | Caswell et al. | 250/227 |
| 4,713,887 | 12/1987 | Kitamura | 33/1 |

FOREIGN PATENT DOCUMENTS

| | | | |
|---|---|---|---|
| 0389019 | 9/1990 | European Pat. Off. | A01H 4/00 |
| 0406132 | 1/1991 | European Pat. Off. | A01G 1/06 |
| 262787 | 12/1988 | Germany | A01G 7/00 |
| 2-295418 | 12/1990 | Japan | A01H 4/00 |
| 2202723 | 10/1988 | United Kingdom | A01G 1/00 |
| WO86/06576 | 11/1986 | WIPO | A01G 7/00 |
| WO92/00004 | 1/1992 | WIPO | A01H 4/00 |

OTHER PUBLICATIONS

Raven et al, eds, (1976) Biology of Plants, pp. 299–300 Worth Publ, Inc. New York, NY.

Primary Examiner—David T. Fox
Assistant Examiner—Elizabeth F. McElwain
Attorney, Agent, or Firm—Pennie & Edmonds

[57] ABSTRACT

There are disclosed a method and a device with which growing points can be cut out of a plant by means of a laser source. The plant is present on carrying means thereby, said carrying means comprising tubes, through which the plant is sucked onto the end face of the carrying means. After the laser source has been switched on the plant is manipulated by means of an XY-table, during which operation the switched-on laser is led along the successive circumferences of bounded areas, within which the growing points are present. The bounded areas have been determined on the basis of the image which is obtained after the contours of the image recorded by image recording means have been determined. When three contour branches intersect the circumference of a bounded area, it is assumed that no growing point is present within said area.

22 Claims, 3 Drawing Sheets

METHOD FOR USE IN A MULTIPLICATION PROCESS OF PLANTS AND A DEVICE FOR CARRYING OUT SAID METHOD

BACKGROUND OF THE INVENTION

The invention relates to a method for use in a multiplication process of plants, whereby an image is made of a plant, which is converted into electronic display data, which are processed in order to determine data with regard to the coordinates of growing points in the image of the plant, said data being used for cutting the growing points out of the plant.

The invention furthermore relates to a device for carrying out said method, said device comprising carrying means for a plant to be cut, image recording means, electronic processing means coupled to said image recording means, said processing means comprising a display device on which image data stored after an image of the plant has been recorded with the image recording means can be visualised, and cutting means connected to the electronic processing means for cutting the plant along a predetermined cutting path.

Such a method and device are known from the international Patent Applications WO 86/06576. By means of a CCD-camera a two-dimensional image is made of plant material present on a continuous belt. The image is digitized and stored in a microcomputer memory. Then the stored data are processed in such a manner that an image in the shape of a co-ordinate representation is produced, in which in particular converging branches are identified as possible junctions. Cutting locations determined by the microcomputer, which are located in the centre of the junctions, or which are present at a distance of 4 mm from the end of a branch. are cut through by means of a rotatable cutting blade which is movable in two directions.

The known method and device have a number of disadvantages. Already at the time of a first contact between the cutting blade and the generally very light plant there is a great risk that the plant is moved and that the actual position of the plant and the junction in particular no longer corresponds with the data stored in the microcomputer. A possible next cutting action will not be very effective in this manner. Moreover, the cutting may readily transmit disease germs from a diseased plant to a plant that is still healthy, which may result in a fast-spreading infection and a great deal of damage, since the infected plants can no longer be used for the culture of tissue in the multiplication process, and new basic plant material must be provided.

The purpose of the invention is to provide a method and a device for use in a multiplication process of plants, with which an effective increase in the production of cut plants can be achieved in that potential growing points in the plant are quickly recognized and cut out on the basis of elements of a plant image.

SUMMARY OF THE INVENTION

In order to achieve that purpose the method according to the invention is characterized in that the process of determining the co-ordinate data of the growing points comprises a partial process, in which the contour in the image data of the plant is determined, and that the image of said contour is searched for bounded areas, whose circumference is intersected by at least three branches of the contour, and in which at least one growing point is assumed to be present.

When using the method according to the invention the contour consists of a relatively small number of image points, in which the information which is relevant for the method according to the invention is concentrated. The advantage of this is that with a given limited speed the electronic data processing of the limited number of image points takes place in a shorter time, as a result of which the yield of the number of plant pans cut in the multiplication process increases.

Although in principle each point of a plant can be regarded as a growing point and some plants can simply be cut into pieces, whereby each piece can develop into a plant, other species cannot be multiplied as easily. The method according to the invention is excellently suited for multiplying the latter plant species, since the method makes it possible to cut out the branch-off points located near the axillae of the plant stems, where most nutrients are located, so that e.g. an in vitro culture on the basis of said cut starting material has a great chance of success.

One embodiment of the method according to the invention is characterized in that prior to looking for the bounded areas, the contour is smoothed, whereby overly strong local orientation changes in the lines of which the contour is composed are averaged and approached by lines having less strong orientation changes.

The advantage of this embodiment is that in this case practically no bounded areas which do not not contain any growing points are identified, because the areas are located near the e.g. crenated circumference of the leaves of some plant species. This has resulted in an improved efficiency when searching for bounded areas that do have a growing point.

A further embodiment of the method according to the invention is characaterized in that the search for bounded areas in particular takes place near places in the image of the contour where a relatively strong orientation change in the contour occurs.

The advantage of this further embodiment of the invention is that this embodiment makes it possible to search more efficiently for areas with a growing point, as a result of which a further reduction in the processing time of a plant in the multiplication process becomes attainable. Furthermore the method lays the foundation of an automatic determination of the bounded areas, and thus of a highly automated cutting process. A very simple embodiment of the method according to the invention has bounded areas which are circular.

Cutting preferably takes place along the entire circumference, or at least along that part of the circumference of the bounded areas which is intersected by contour branches.

When carrying out the method according to the invention the plant is preferably sucked down.

The advantage of this is that thus a good position of the plant is maintained, regardless of the type of cutting means which is being used.

It is especially preferred to carry out the cutting operation by means of a beam of electromagnetic rays.

The advantage of this is that said cutting can take place quickly and without direct contact, as a result of which the risk of infection of the cut plants is minimized, thus ensuring the good quality of the final product. Furthermore it is advantageous that it is prevented that the delicate plant cells are crushed, since practically no force is exerted on the plant during the cutting operation, and thus the plant will not show a tendency to move during cutting. Furthermore it is advantageous that at the location of the cutting face the cutting wound is seared up and that it slightly hardens, as a result of which it is largely prevented that vulnery fluid gets out and that disease germs get in. The growing process and the properties of next generations of plants appear not to be affected by cutting by means of the beam of electromagnetic rays.

The device according to the invention for carrying out the method is characterized in that the electronic processing means comprise a comparator circuit coupled to the memory, in which successive grey values stored in said memory locations, which correspond with adjacent picture elements on the display device, are compared with each other, and an image point, whose grey value is significantly different from the grey value of an adjacent image point forming part of the background of the image on the display device, is regarded as an image point which forms part of the plant contour.

Generally the contour or, if desired, the entire plant image can be displayed in colour on the display device. A very simple embodiment of the device according to the invention provides bivalent grey values, so as to display the colours white and black.

A further device according to the invention is characterized in that the device comprises a light pen coupled to electronic processing means, which can be moved across the display tube of the display device, said light pen marking the bounded areas and then supplying the image data of the bounded areas to the electronic processing means.

The advantage of this method is that the device works semi-automatically, whereby a cutting path along the circumference of the bounded areas can be plotted by means of the light pen in a very simple manner, on the basis of which the growing points can be cut out of the plant.

A further embodiment of the device according to the invention is characterized in that the carrying means comprise tubes which are placed side by side, and that the device has suction-pressure means connected to the end of said tubes so as to suck or blow, as the case may be, a plant onto or off the other end of the tubes.

The advantage of the device according to the invention is that not only the plants can be sucked in, but that after termination of the cutting operation the cut plants, insofar as desired, can be blown off and carried along by means of the same device having tubes.

Preferably the device according to the invention has a laser device coupled to the electronic processing means, said laser device making it possible to cut, by means of the laser beam delivered by said device, sufficient plant material, in particular along the predetermined circumference of the bounded areas, in a very hygienic, efficient and fast manner.

The laser device, which is generally disposed directly above the carrying means, preferably contains a $CO_2$ laser, which operates in a very advantageous manner in practice.

According to a further preferred embodiment the device according to the invention is characterized in that the positions of the tubes are recorded by the image recording means and stored in the memory, and that the electronic processing means are arranged such that when determining the cutting path to be followed said cutting path does not intersect any tubes.

With an eye to the purpose of the invention formulated earlier, a further procedure is characterised by the fact that an image of the plant is determined on the basis of a signal emitted from a heat-sensitive camera and that, in the heat-image thus formed, concentration-areas of image-points are sought, which concentration-areas are associated with the growth-points of the plant.

The advantage of this further procedure according to the invention is that profitable use can be made of the notion that, in the growth-points of the plant in particular, chemical processes occur which cause heat to be liberated. The sources of the associated liberated thermal radiation at the site of the growth-point manifest themselves in the heat-image of the plant in the form of concentration-areas which are observed by the camera and whose coordinate-data render the locations of the growth-points of the plant which are to be cut out.

The invention and its further advantages will be explained in more detail hereafter, with reference to the accompanying drawing.

DETAILED DESCRIPTION OF THE INVENTION

Figure 1:
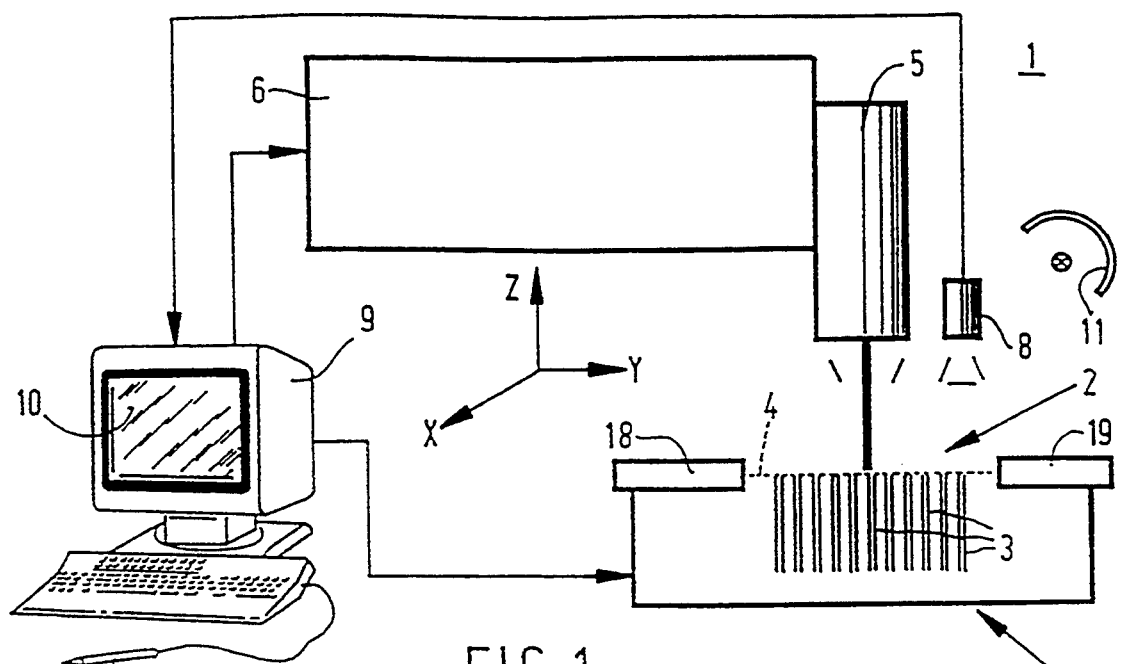
FIG. 1 is a diagrammatic illustration of an embodiment of a device according to the invention, by means of which also the method according to the invention will be explained.

FIG. 1 shows a device 1, which constitutes a link in the multiplication process of plants. The device 1 takes care of the cutting of the plant, whereby in particular the growing points of the plants are cut out. The growing points of a plant are located in particular near the axillae of the plants and at the ends of the plant (see FIG. 3 in this respect). The method to be described in particular relates to determining the individual growing points with the various species, determining closed areas, within which a growing point is located, determining, if necessary, the shortest route from the one closed area to the other, and then cutting out the growing points along the circumference of the closed areas. For that purpose the device 1 has positioning means in the shape of grip-holding means to be described hereafter or, e.g. in the shape of carrying means 2, on which the plant (not shown) is to be provided by means not shown. The carrying means 2 are preferably in the shape of suction-pressure means, and in particular have tubes, a few of which are shown at 3 in FIG. 1. Said tubes 3 are open at both ends. At one end the tubes 3 terminate in an end face 4, which is flat in the illustrated embodiment. The plant (not shown) is to be deposited on said end face 4, after which the plant is sucked down onto said end face 4 by suction means.

In one embodiment (not shown) the plant may also be sucked into a funnel-shaped tube, whereby the stem of the plant is to be inserted into the narrowing part of the funnel.

The device 1 furthermore comprises cutting means which are disposed substantially perpendicularly above the carrying means 2. In the preferred embodiment illustrated in FIG. 1 said cutting means are built up of a laser source 5 and a laser control unit 6 coupled thereto. Since the laser source 5 and the laser control unit 6 are generally rather voluminous, the carrying means 2 are preferably movable in case a laser device is used, e.g. by means of an XY-table 7. In this case it is not necessary to provide a possibility for moving the table 7 in the Z-direction. The table 7 can be moved in the XY plane by means of suitable motors, e.g. in the shape of stepper motors 18 and 19. Such a table 7 can also be used when the cutting means are equipped with conventional cutting means, e.g. comprising a rotating cutting blade or a moving ribbon.

The device 1 furthermore contains image recording means, which e.g. comprise a CCD-camera 8. The camera 8, the laser control unit 6 and the stepper motors 18 and 19 are each coupled to a microcomputer 9 incorporated in the device 1, in which microcomputer the method to be explained hereafter is implemented. In the microcomputer 9 electronic processing means are present, which are provided with a display device 10, on which the image of a plant can be visualized after said image has been recorded by means of the camera 8. For that purpose the camera 8 is connected to electronic processing means provided with a memory, from which memory the image data written by the camera 8 can be read.

If necessary the device 1 furthermore contains lighting means 11, which emit light of a required frequency and intensity. The polarisation of the light delivered by the lighting means 11 is preferably circular. A polarisation filter may be placed in front of the camera 8, so that the camera does not detect any interfering reflections. Such interfering reflections e.g. relate to reflections of the carrying means 2 back to the camera 8, or to reflections from the vulnery fluid at the location where the plant has already been cut.

Generally the operations on the plant will have to take place in a sterile environment, since otherwise the risk of infections will be too high. For that purpose in particular the carrying means 2 will be surrounded by means (not shown) within which sterility is maintained.

Since there is no mechanical contact between the laser source 5, the laser beam delivered by said laser source, and the plant, the demands to be made of said means will be less severe if use is made of a laser source 5.

The laser source 5 is e.g. a McZ, a YAG or, on account of the low purchasing cost, preferably a $CO_2$ laser. The laser has a power of e.g. 500 Watt, and delivers a laser beam having a fixed frequency and a generally controllable output. The output to be adjusted depends on the required cutting speed, the thickness of the plant stem and the degree of desiccation required when cutting along the cutting face. The degree of convergence of the laser beam will be adjustable by means of a system of lenses which will not be explained in more detail. Preferably the laser is not operated in pulses, because in that case higher cutting speeds are attainable.

The laser beam has a suitable, e.g. circular polarisation and is preferably transversally electromagnetic. In such a TEM mode the stability appears to be sufficient, also when low outputs are used. If required the laser beam may also be surrounded by a protective gas, by means not explained. When the plant is being cut said protective gas functions in particular to prevent oxidation of the wound surface of the plant. Suitable protective gases include: argon, pressurized air, nitrogen, but also oxygen.

After the plant, possibly stripped of its leaves, has been deposited on the end face 4 of the tubes 3 and is sucked down, the images recorded by the camera 8 are transmitted to the microcomputer 9 for further processing. Each of the picture elements of which the image is composed is thereby stored in a predetermined memory location of the memory incorporated in the data-processing means. In particular the so-called grey value of each image point is stored in a memory location.

Figure 2:
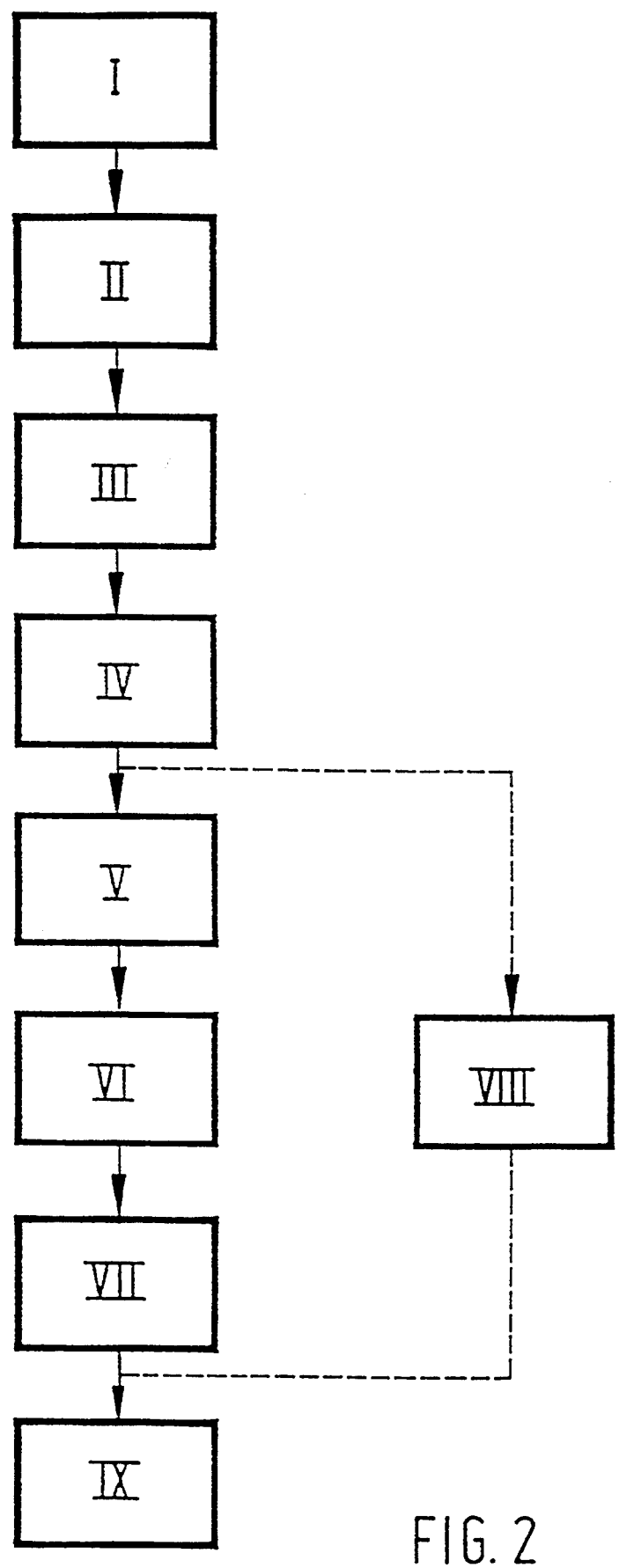
FIG. 2 is a flow chart in explanation of a preferred embodiment of the method according to the invention.

The flow chart of FIG. 2 shows in a block diagram the successive steps to which the image information stored in the memory is subjected.

The various steps are indicated by means of Roman numerals in the blocks of FIG. 2. Their meaning is as follows:

I Picture elements are subjected to a, possibly parameterized, threshold operation, so as to display the image of the plant e.g. in black and white with respect to the background.

II Loose picture elements or clustered picture elements are removed from the image. Furthermore small, non-continuous images of plant pans having a width of e.g. 1 or two picture elements, are not displayed.

III In this step the contour of the plant image is determined. This contour is present at those locations where image points from the background and image points adjacent thereto have significantly different grey values. For example where white background image points blend into black image points of the plant, or possibly the other way round.

IV The contour is filtered, during which operation local short deviations in the contour are replaced by local straight lines.

V Searching for places with strong orientation changes takes place, by first comparing the derivatives of contour lines with each other. It is hereby tested whether the angles between the contour lines are smaller than e.g. 90° or 120°.

VI Around the places with strong orientation changes bounded areas can be indicated. Said bounded areas bounded the plant structure located therein, which plant structures may e.g. have an H- or a Y-structure. Moving along the circumference of the bounded areas the number of black/white transitions is counted. Each registered transition points at the circumference of the bounded area in question being intersected by a plant contour. When six or more transitions are counted it is assumed that at least one Y-structure is present, on the basis of which it is assumed that a growing point is present within the bounded area in question.

VII During this step it is ascertained whether a bounded area that is detected belongs to a bounded area already found before.

VIII Alternatively the automatic determination of the bounded areas, as described with reference to blocks V, VI and VII and indicated on the display device 10, is replaced by manually inputting, by means of a light pen, the bounded areas which are assumed to contain a structure having at least one growing point.

IX The co-ordinate data of the circumference of the bounded areas is changed in such a manner that account is taken of the location of the tubes 3 on the carrying means 2. The revised coordinate data of the circumference of the bounded areas constitute the data which the control of the XY-table 7 and the laser control unit 6 will be based on.

FIG. 1 shows at 12 a light pen, which is otherwise generally known. Indicating the bounded areas on the display device by means of the light pen 12 renders the method in question semi-automatic, since each cutting action still requires an operator to interpret the plant image in question, and to indicate the bounded area or areas.

Figure 3:
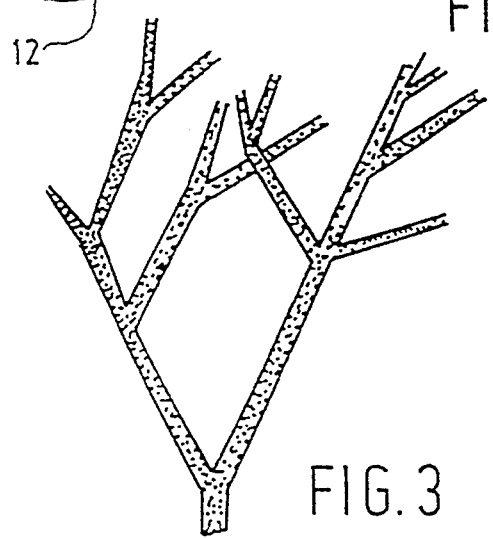
FIG. 3 is a representation of a plant, whose growing points are to be cut out.

FIG. 3 shows in black and white the image recorded by the camera 8, which can be visualised on the display device 10. The grey values of the image points of which the image is composed are bivalent in this case, since the image contains white or black image elements.

Figure 4:
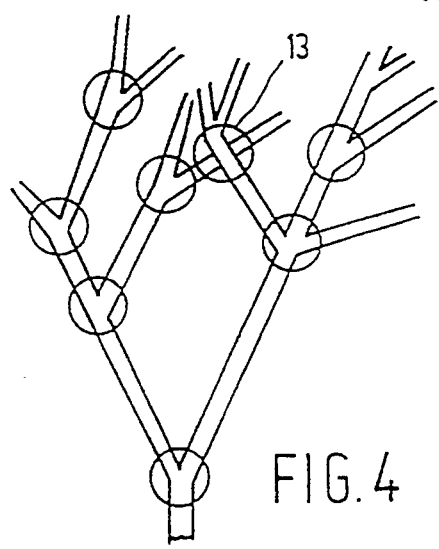
FIG. 4 is a representation of a contour registration of the plant of FIG. 3, in which the growing points are encircled.

FIG. 4 shows the contour image composed on the basis of the image illustrated in FIG. 3, in which circular bounded areas are depicted by way of illustration. A growing point is assumed to be present within each of the bounded areas. A bounded area indicated at 13 does not have a growing point, however, in spite of the fact that an X-structure is present within said area. Intersecting branches of the plant are namely present within the bounded area 13. The effectiveness with which the growing points within a bounded area can be identified can be further enhanced when the camera 8 is a stereo camera. By means of suitable processing of the stereo images it is possible, when comparing the image recorded by each of the cameras in question, to conclude that the structure in question indeed has overlapping branches and that the presence of a growing point in the bounded area is not assumed, therefore, or that this is not the case, and that a growing point is indeed present in the bounded area in question.

Figure 5:
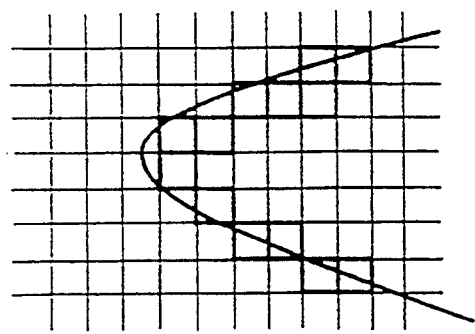
FIG. 5 is a partial representation of a plant contour according to FIG. 3, by means of which the contour registration of FIG. 4 will be explained.

FIG. 5 serves to illustrate the manner in which the contour image of FIG. 4 is created from the image of FIG. 3. In a comparator circuit incorporated in the electronic processing means a comparison is respectively made of the grey values of those memory locations that correspond with adjacent picture elements on the display device. If there is a significant difference between the contents of the memory locations, then the image point which is different from a background image point is an image point which belongs to the contour. Image points that belong to the contour have a darker frame than image points which belong to the background or which belong to the actual image of a branch of the plant. As already explained, a smoothing operation may be carried out on the image points which are considered to belong to the contour, if required, so as to slightly smoothe local knurls in the contour image caused by displaying the leaf edges.

Figure 6:
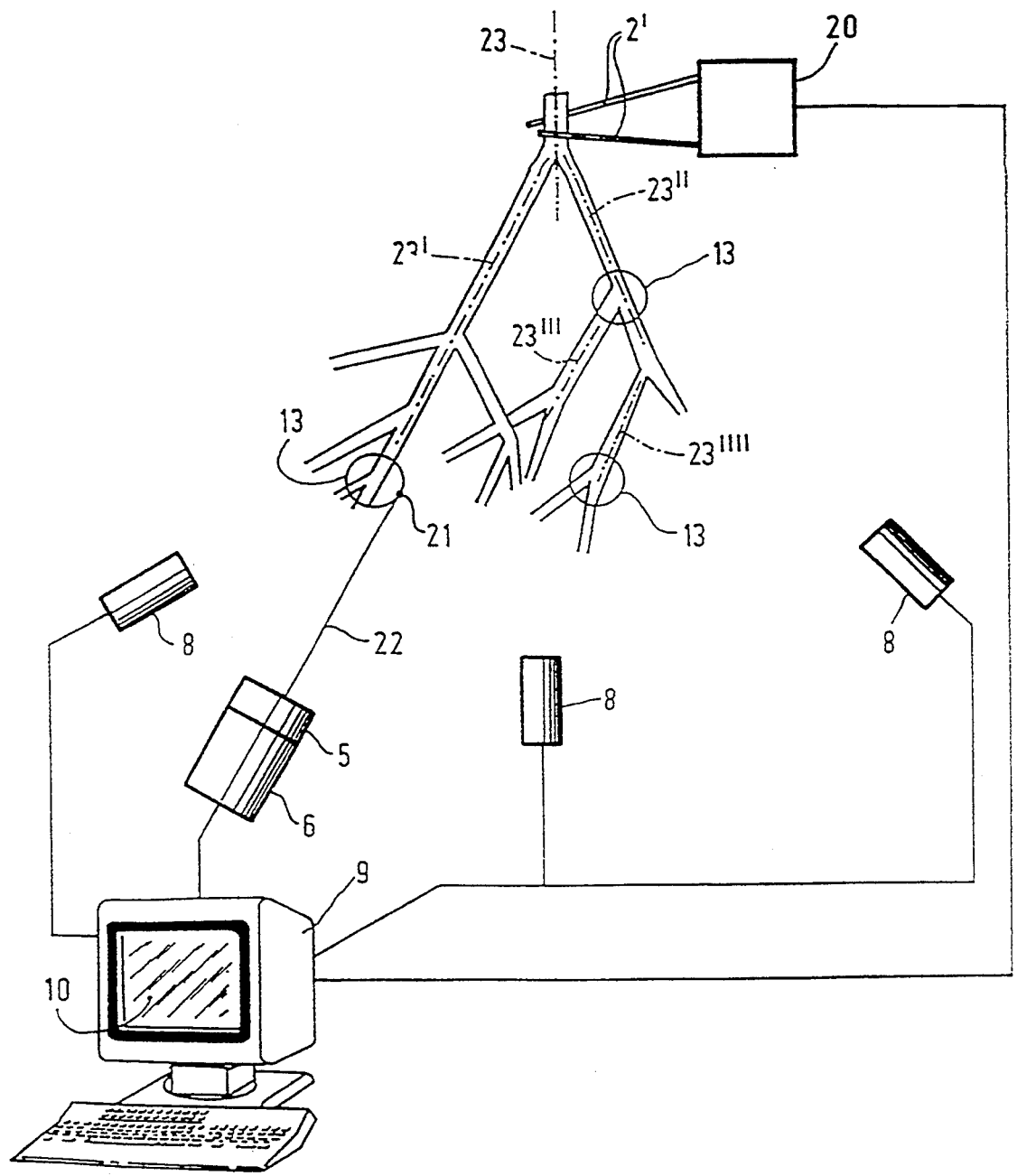
FIG. 6 is a diagrammatic representation of a preferred embodiment of the device according to the invention.

Preferably the positioning means are in the shape of grip-holding means 2' (see FIG. 6), which grip the plant at its bottom side. The grip-holding means 2' form e.g. part of a robot arm 20, and can be put in required positions at the command of a suitable control system of the microcomputer 9 in that case. The grip-holding means are preferably able to hold the plant in an upside down position. In this position a two- or three-dimensional image of the plant can be made by means of one or more cameras 8 arranged spaced from each other, on the basis of which a corresponding contour representation can be composed, in which the bounded and, in case a three-dimensional image is used, spacial areas can be selected, the circumferences of which, dependent on the direction in which the image is studied, provide the co-ordinate data on the basis of which the growing point in question is cut out by means of the laser spot 21 of the laser beam 22.

In certain circumstances the positioning means in the shape of e.g. the carrying means 2 or the grip-holding means 2' may be moved during the cutting operation. Moving the laser spot is relatively costly, but it can be quickly effected by moving the mirrors directing the laser beam, whilst putting the positioning means into motion is a relatively slow process, which is comparatively easy to realise, however, by means of a common controllable robot arm 20. The situation whereby in the upside down position of the plant both the laser spot 21 and the robot arm 20 are moved is to be preferred. After having been cut out the growing points will fall down individually, as a result of the force of gravity. It is especially preferred to design the grip-holding means such that they are rotatably movable about one or more axes 23, 23', 23'', 23''', 23'''', in which case furthermore the generally limited speed of motion of the positioning means is compensated in a manner which is acceptable in practice. By rotating about said axes during cutting the bounded areas 13 can be cut out in a simple manner. Particularly when multi-dimensional images of in particular the contour of the plant are available the coordinates of the axes 23, 23', 23'', 23''', 23'''', can be determined in a mathematical manner in the computer 9.

Of course several cutting devices in a time-division mode may use one and the same laser source 5. In that case devices to be operated in parallel are formed, in which cutting takes place by means of one and the same laser source 5. Furthermore it is noted that in case of an interactive dialogue with the microcomputer 9, in which use is made of a light pen 12, a so-called mouse may alternatively be used. Furthermore it is noted that in case the plant in question is sucked into a funnel-shaped container, the possibility of overlapping branches in the image of the camera 8 is indeed reduced, but that in that case special measures have to be taken to prevent that non-desired plant parts are cut as well, as a result of laser beam reflections on the funnel interior. In that case the inner surface of the funnel should be covered with a material which is able to absorb the laser beam, or not to reflect it, as the case may be, without melting thereby.

In principle young plants of the most widely varying species can be cut using the above-described method and device. In particular vegetable plants, flower plants and trees are mentioned in this respect. Successful experiments have been carried out with e.g. asparagus, but also with roses, asters, callatea, eucalyptus, fern, birch, statice, cordoline and many other species.

In an alternative embodiment of the invention, the image recording means in the form of the camera 8 are embodied with a heat-sensitive camera. In this case, application of the illumination means 11 is unnecessary because, based on the heat-image which can be composed on the basis of the signals emitted by the heat-sensitive camera 8, a direct view arises regarding the actual positions of the various growth-points, this being due to the presence in the growth-points of chemical processes which emit thermal radiation and manifest themselves to the heat-sensitive camera 8 in the form of concentration-areas. In that case, the coordinate-data of the concentration-areas directly determine the locations of those growth-points of the plant which are to be cut out. It is clear that, in that case, the creation of a contour-image of the plant is made redundant, along with any possible accompanying image-smoothing process. In principle, making a three-dimensional image of the plant is also rendered unnecessary, at least in the case whereby both the laser and the heat-sensitive camera are located above the plant. This has its origins in the fact that, when applying the heat-sensitive camera, the ability to see depth in the image of the plant is not a prerequisite to cutting out the growth-points. It follows immediately that this has a considerable influence on the calculation-time of the electronic processing means 9.

I claim:

1. A method for use in a multiplication process of plants, whereby an image is made of a plant, which is converted into electronic display data, which are processed in order to determine data with regard to the co-ordinates of growing points in the image of the plant, said data being used for cutting the growing points out of the plant, characterized in that the process of determining the co-ordinate data of the growing points comprises a determination of only the contour in the image data of the plant, and that the image of said contour is searched for bounded areas, said bounded areas being areas whose circumference is intersected by at least three branches of the contour, and in which at least one growing point is therefore assumed to be present; which method further comprises cutting loose the plant parts containing said growing points.

2. A method according to claim 1, characterized in that prior to looking for the bounded areas, the contour is smoothed, whereby overly strong local orientation changes in the lines of which the contour is composed are averaged and approached by lines having less strong orientation changes.

3. A method according to claim 1, characterized in that the search for bounded areas in particular takes place near places in the image of the contour where an orientation change describing an angle of less than 120° in the contour occurs.

4. A method according to claim 1, characterized in that the bounded areas are circular.

5. A method according to claim 1, characterized in that cutting takes place along at least part of the circumference of the bounded areas.

6. A method according to claim 1, characterized in that cutting takes place at the location where the circumference of the bounded areas is intersected by contour branches.

7. A method according to claim 1, characterized in that the plant is turned upside down, and while the plant is held upside down the plant parts containing growing points are cut loose.

8. A method according to claim 1, characterized in that said method comprises sucking down the plant.

9. A method according to claim 1, characterized in that the cutting operation is carried out by means of a beam of electromagnetic rays.

10. A device for use in a multiplication process of plants, comprising positioning means for positioning a plant to be cut, image recording means, electronic processing means coupled to said image recording means, said processing means comprising a display device, on which image data stored after an image of the plant has been recorded with the image recording means can be visualized, and cutting means connected to the electronic processing means for cutting the plant along a predetermined cutting path, characterized in that said electronic processing means comprise a comparator circuit coupled to the memory, in which successive grey values stored in said memory locations, which correspond with adjacent picture elements on the display device, are compared with each other, and an image point which forms part of the plant contour is selected to be an image point whose grey value is significantly different from the grey value of an adjacent image point forming part of the background of the image on the display device.

11. A device according to claim 10, characterized in that the grey values are bivalent.

12. A device according to claim 10, characterized in that the device comprises a light pen coupled to electronic processing means, which can be moved across the display tube of the display device, said light pen marking the bounded areas and then supplying the image data of the bounded areas to the electronic processing means.

13. A device according to claim 10, characterized in that the positioning means are carrying means, on which the plant to be cut is to be deposited, and that the carrying means comprise tubes which are placed side by side, and that the device has suction-pressure means connected to the end of said tubes so as to suck or blow, as the case may be, a plant onto or off the other end of the tubes.

14. A device according to claim 13, characterized in that said carrying means are mounted on a controllable XY table coupled to the electronic processing means.

15. A device according to claim 10, characterized in that said positioning means are grip-holding means.

16. A device according to claim 10, characterized in that the device has a laser device coupled to the electronic processing means.

17. A device according to claim 16, characterized in that said laser device contains a $CO_2$ laser.

18. A device according to claim 13, characterized in that said laser device is located perpendicularly above the carrying means.

19. A device according to claim 13, characterized in that the positions of the tubes are recorded by the image recording means and stored in the memory, and that the electronic processing means are arranged such that when determining the cutting path to be followed said cutting path does not intersect any tubes.

20. A device according to claim 16, characterized in that said laser device is located under the positioning means in the shape of grip-holding means.

21. A device according to claim 20, characterized in that said image recording means are located under said grip-holding means.

22. A device according to claim 20, characterized in that if the grip-holding means take a position in which the plant is held upside down, said grip-holding means are rotatable about at least one axis.

* * * * *